(12) United States Patent
Qiu et al.

(10) Patent No.: US 7,030,633 B1
(45) Date of Patent: Apr. 18, 2006

(54) FOUR-TERMINAL METHODS FOR RESISTIVITY MEASUREMENT OF SEMICONDUCTING MATERIALS

(76) Inventors: Chunong Qiu, 3590 Ovide St., Brossard, Quebec (CA) J4Y 2N2; Cindy X. Qiu, 6215 Bienville St., Brossard, Quebec (CA) J4Z 1W6; Steven Shuyong Xiao, 514B St-Luc, Laval, Quebec (CA) H7N 4Y3

( * ) Notice: Subject to any disclaimer, the term of this patent is extended or adjusted under 35 U.S.C. 154(b) by 0 days.

(21) Appl. No.: 11/002,936

(22) Filed: Dec. 3, 2004

(51) Int. Cl.
*G01R 31/26* (2006.01)

(52) U.S. Cl. .................. 324/754; 324/763; 324/765

(58) Field of Classification Search ............... None
See application file for complete search history.

(56) References Cited

U.S. PATENT DOCUMENTS

| | | | | |
|---|---|---|---|---|
| 4,516,071 | A | * | 5/1985 | Buehler .................. 324/765 |
| 5,552,718 | A | * | 9/1996 | Bruce et al. ............ 324/765 |
| 6,118,137 | A | * | 9/2000 | Fulford et al. ........... 257/48 |
| 6,836,140 | B1 | * | 12/2004 | Fujikawa et al. ........ 324/770 |

* cited by examiner

*Primary Examiner*—Minh N. Tang

(57) ABSTRACT

This invention provides an innovative multi-line structure and an effective four-terminal method for the resistivity measurement of semiconductor materials. The multi-line structure and the four-terminal method not only allow one to perform resistivity measurement on any inorganic and organic semiconductor thin film conveniently, rapidly and accurately but also offer the means to study resistivity uniformity across the semiconductor thin film.

20 Claims, 10 Drawing Sheets

US 7,030,633 B1

FOUR-TERMINAL METHODS FOR RESISTIVITY MEASUREMENT OF SEMICONDUCTING MATERIALS

FIELD OF THE INVENTION

This invention relates to methods to characterize semiconductors in general and organic semiconducting materials in particular for electronic and optoelectronic applications. More specifically, it relates to multi-line structures and four-terminal measurement methods for standardized resistivity measurements of semiconducting materials, and the method to prepare the multi-line structures.

BACKGROUND OF THE INVENTION

The discovery of metal-like electrical properties of polyacetylene when exposed to oxidizing agents like iodine vapor in 1977 by Shirakawa, Heeger and MacDiarmid introduced of a group of new members into the semiconductor family—the organic semiconductors and earned the discoverers the Nobel Prize for chemistry in the year 2000. This discovery created a tremendous opportunity as the organic semiconductors exhibit a combination of properties of metals and plastics, being conductive and flexible at the same time. Since then, efforts of the industry and research groups have been made on synthesis of new organic semiconductors and on studying their properties for different applications.

Various electronic and optoelectronic devices have been developed using small molecules organic semiconductors or conducting polymers. Some examples are: organic light emitting devices (OLEDs), organic thin film transistors (OTFTs) and organic solar cells. Compared to devices and circuits fabricated using inorganic semiconductors such as silicon (Si) or gallium arsenide (GaAs), the organic devices and circuits have the advantages of low fabrication cost, large substrate area and flexibility. Possible applications of the organic devices include: light sources, electronic displays, circuits, photovoltaic energy conversion and optical signal detection.

One of the most important electronic properties of the organic semiconductors is the electrical resistivity (or conductivity) of the materials. Many factors govern the electrical resistivity of an organic material, such as polymeric structure, molecular size and impurities. The electrical resistivity also depends on whether or not and how much a dopant is introduced in the material.

Usually, device engineers need to know beforehand the properties of the semiconductor materials in order to design and construct devices like light emitting diodes (LEDs) and solar cells with superior performances. Semiconducting material producers therefore are required to supply their customers with the resistivity of their semiconducting materials. On the other hand, the obtained resistivity results will help material scientists to adjust their synthesis process to obtain organic semiconducting materials with electrical resistivity (or conductivity) in the desired ranges. Unfortunately, the electrical conductivity values reported by material manufactures vary widely from the actual values, caused by lack of a standardized resistivity measurement method. These added uncertainties will make it more difficult for the device engineers to design and simulate device structures.

Conducting organic materials supplied by manufactures today are normally in forms of chunks (solid form). In the case of conducting polymers, they sometimes are dissolved in popular solvent (liquid form). It is almost impossible to determine the resistivity of an organic semiconductor in chunks. For polymers in liquid form, because most of undoped polymers are not good conductors, it is rather difficult to accurately measure the resistivity of polymers in a liquid. Furthermore, the resistivity values of polymers quoted at different concentration and dissolved in different solvents also add confusion in the already vague specification sheet of conducting polymers.

The traditional four-point probe measurement method has been used routinely for the evaluation of resistivity of thin films semiconductors in the inorganic semiconductor industry. This method is accurate and easy to use. However, due to the large resistivity of undoped organic semiconducting materials and high contact resistance presenting between the metal probes and the thin organic films, the current that can pass through an organic semiconducting film through the needle probes is extremely small and not easy to measure, hence, the traditional four-point probe method ceases to be an effective way of evaluating the resistivity of an organic semiconducting film.

From the above-stated comments, it is clear that a structure and a method for standardized resistivity measurements are in need for semiconductors in general and for organic semiconductors in particular. This method should be accurate and easy to use and should provide an effective and standardized tool for both material scientists and device engineers.

OBJECTIVE OF THE INVENTION

One objective of this invention is to disclose four-line structures for standardized resistivity measurement of semiconductors. One other objective is to disclose multi-line structures for resistivity measurement of semiconductors. Another objective is to provide a four-terminal method to accurately measure resistivity of semiconductor thin films using the four-line and the multi-line structures. Still another objective is to provide methods to evaluate resistivity uniformity of semiconductor thin films using the multi-line structures. Yet another objective is to provide means to reduce the contact resistance between the conducting lines in the structures and the semiconductors.

DETAILED DESCRIPTION OF THE PREFERRED EMBODIMENT

Traditional Four-Point Probe Resistivity Measurement Method

Figure 1:
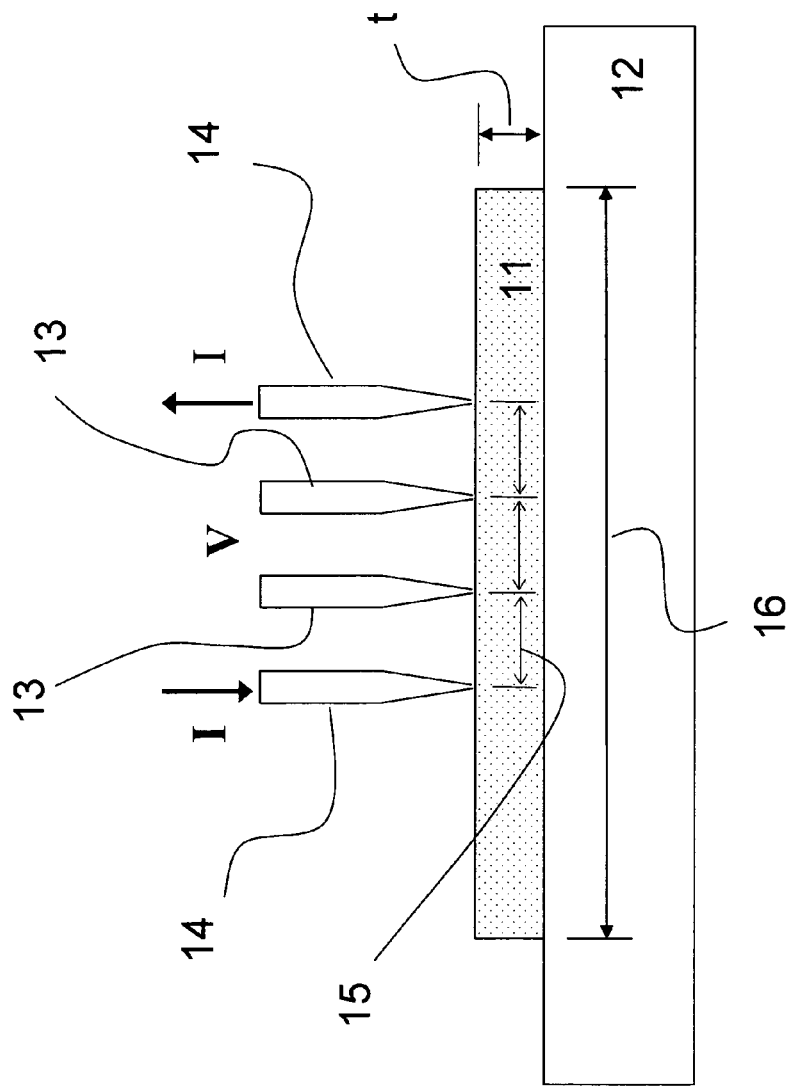
FIG. 1 a schematic diagram showing the traditional four-point probe measurement setup.

The traditional four-point probe resistivity measurement setup (10) is shown in FIG. 1, where a semiconductor thin film (11) is coated on an insulating substrate (12) and four steel needles (13, 14) are positioned on top of the thin film (11) with an equal distance (15) between adjacent needles. During the measurement, the four needles (13, 14) are brought down to make a contact with the thin film (11) and a constant current (I) is applied to the two outer needles (14). The voltage (V) between the inner two needles (13) then is measured using a voltmeter. For a semiconductor film (11) with a thickness (t) much smaller than either the width (16) or the length (not shown) of the film (11), the sheet resistance is given by $$R_S = CF \cdot \frac{V}{I} \ \Omega/\text{square} \quad (1)$$

where CF is the correction factor. When the width (16) of the film (11) is much greater than the space (15), the correction factor is equal to 4.54. The resistivity of the film (11) is given by $$\rho = R_S \cdot t = 4.54 \cdot \frac{V}{I} \cdot t \ \Omega\text{-cm} \quad (2)$$

The resistance values of organic semiconducting materials are generally much higher (few orders of magnitude higher) than that of the inorganic semiconducting materials. This is especially true for the undoped organic materials. It is not uncommon to see resistivity of an undoped organic material in the range of a few tens of $M\Omega$-cm (conductivity in the range of $10^{-8}$ S/cm). On top of that, the needles (13, 14) in the four-point probe setup (10) are made of steel, which create another problem for the measurement—extremely high contact resistance between the four needles (13, 14) and the film (11). This high contact resistance is caused by two factors: a small contact area between the needle tip and the films, and a non-adjustable work function difference between the two materials (steel and organic semiconductor). Limited by the structure and material of the needles (13, 14), the large contact resistance cannot be reduced either by enlarge the contact area or by choosing different probe materials according to the organic materials to be measured.

Due to the large resistivity values of the organic semiconductor films and the large contact resistance between the probe needles and the semiconductor films, the current that can pass through the film (11) between the two outer needles (14) is extremely small and difficult to measure. As a result, the above-mentioned traditional four-point probe method is no longer practical for evaluation of the conducting organic films.

Therefore, it is evident that a new structure is in need to replace the traditional four-point probe setup for the resistivity evaluation of thin film semiconductors especially for organic semiconductors. First of all, this structure should have the advantages of the traditional four-point probe setup, which allow one to carry out resistivity measurements easily and accurately. Secondly, it should provide an enlarged contact area between the metal and the semiconductor thin film to reduce the contact resistance, and it should also have the option to choose different materials for construction of the structures according to the semiconductors to be studied so that the contact resistance can be further reduced. Moreover, standard four-terminal measurement methods to accurately determine the electrical resistivity and the uniformity of a semiconductor, especially an organic semiconductor are also needed.

Four-Line Structures for Four-Terminal Resistivity Measurement

Refer now to FIG. 2(a), where a schematic top view of a testing chip (20) with a four-line structure (referred as four-line structure (20) in the following description), according to one embodiment of the invention is shown. The four-line structure (20) consists of an insulating substrate (21); two outer conducting lines (22); two inner conducting lines (23); two outer contact pads (24) and two inner contact pads (25). The outer conducting lines (22) are connected to outer contact pads (24) and the inner conducting lines (23) are connected to the inner contact pads (25), through a connection section (26, 27). The inner and outer conducting lines (22, 23) are parallel to each other, and having a same length ($L_a$), a same line width ($W_L$), and an identical spacing ($W_S$) between adjacent lines.

In FIG. 2(b), a cross-sectional view of the four-line structure (20) taken along the line A—A' is shown. In this Figure, a semiconductor thin film (29) of a thickness (t) is also present. To carry out a four-terminal resistivity measurement, this semiconductor thin film (29) can be applied onto (20) by vacuum deposition methods, including thermal evaporation, sputtering, chemical vapor deposition and molecular beam epitaxial, or by non-vacuum methods, including spin coating, spray, screen printing, ink jet printing and chemical bath deposition. The semiconductor film (29) to be tested should cover at least the active area (28), defined by a length that is equal to the length ($L_a$) of the conducting lines (22, 23) and a width ($W_a$) that is equal to the combined width ($4 W_L + 3 W_S$) of the four conducting lines (22, 23) and all the spacings. The thickness (t) of the semiconductor thin film (29) should be much smaller than either the length ($L_a$) or the width ($W_a$) of the active area (28). In order for the measurement to be accurate, the ratio of the spacing ($W_S$) to the line width ($W_L$) should be greater than 5 (more preferably between 10 and 20).

As shown in FIG. 2(b), the conducting lines (22, 23) are having the same thickness ($t_L$). However, a four-line structure for four-terminal resistivity measurement can also be constructed with different thickness for the conducting lines. The thickness of the ducting lines is selected in the range between 0.1 and 10 μm, preferably between 0.5 and 5 μm. This thickness should be selected to provide a small enough resistance for the conducting lines.

In the four-line structure (20), the contact area between the conducting lines (22, 23) and the semiconductor thin film

(29) is much greater than the tip area of the needles (13, 14) in the traditional four-point probe setup (10 in FIG. 1), therefore, the contact resistance between a four-line structure (20) and a semiconductor is greatly reduced.

In order to further reduce the contact resistance, the four-line structure (20) can be prepared using different metals having different work functions to best suit the organic semiconductors to be tested. For example, instead of using gold (Au) for the conducting lines (22, 23), silver (Ag) or titanium (Ti) can be used to reduce the contact resistance between the conducting lines (22, 23) and organic semiconductor $Alq_3$. Other than metals, electrically conducting metal oxides such as indium tin oxide (ITO), zinc oxide (ZnO) and cadmium sulfide (CdS) can also be used to form the conducting lines (22, 23). The conducting lines can be formed by a vacuum deposition process followed by a lift-off or an etching process. The lines can also be prepared by a non-vacuum method. The substrate (21) can be any non-conducting substrates including glass plates, ceramic, plastic plates, plastic sheets etc. It can also be semiconductors or metal substrates with an insulating coating on top.

The four-line structure (20) not only allows one to evaluate resistivity of organic semiconductors quickly and accurately, it also provides a standardized tool to both material scientists and device engineers. The four-line structure (20) is intended to be used by the material scientists or chemists to check quickly the resistivity value of each batch of samples and make sure the shipped polymer has a resistivity value within the specification of their products. Device engineers can also use the four-line structure (20) to examine their polymers before the actual device fabrication process. The four-line structure (20) is inexpensive and can be used as disposables. It can also be reused if the semiconductor thin film can be removed easily (like in the case of conducting polymers).

Figure 2:
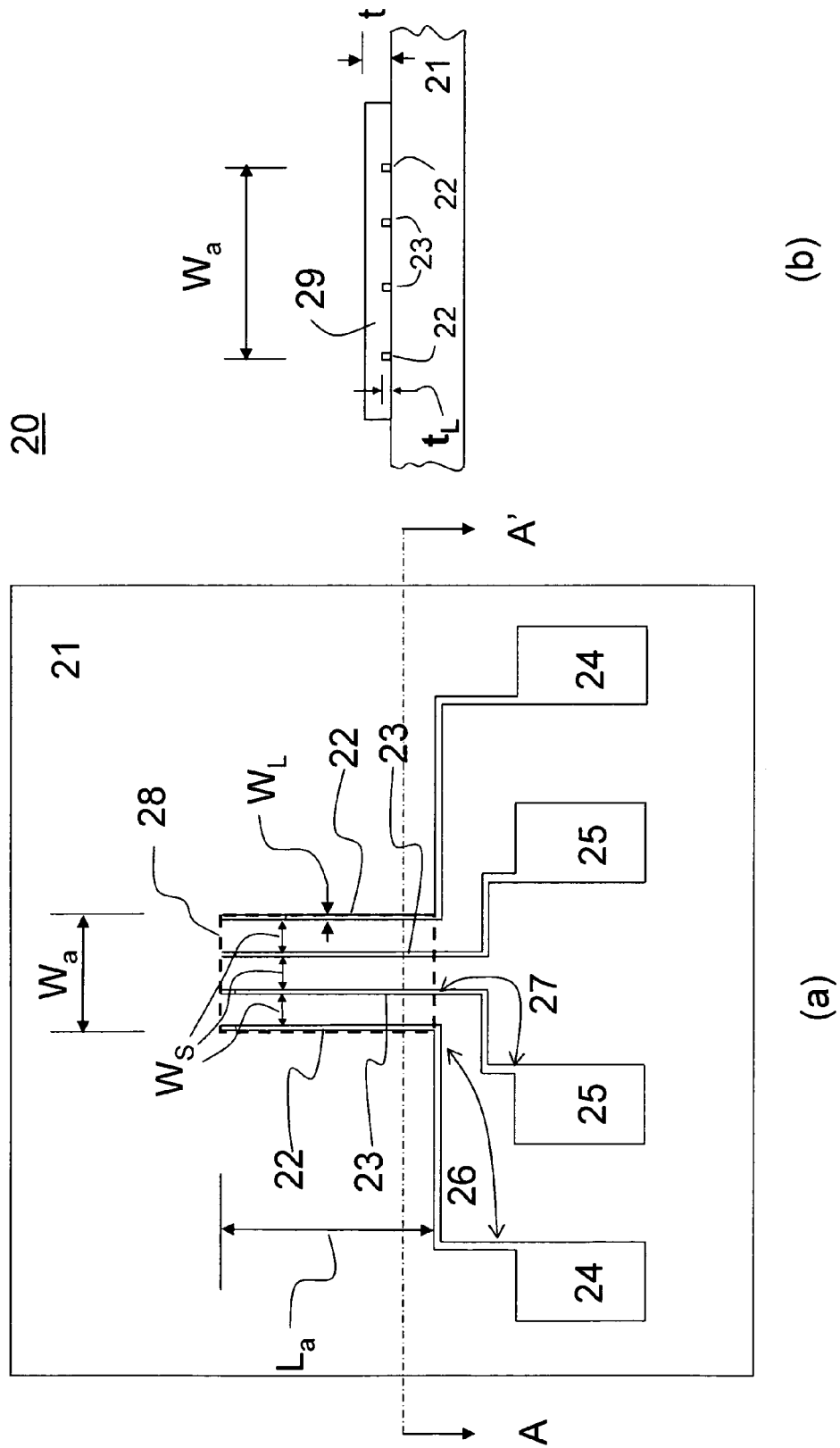
FIG. 2 (a) shows a schematic top view of a four-line structure (20) for four-terminal resistivity measurement according to one embodiment of the invention, and (b) shows the cross-sectional view of the four-line structure (20) coated with a layer of semiconductor (29).
Figure 3:
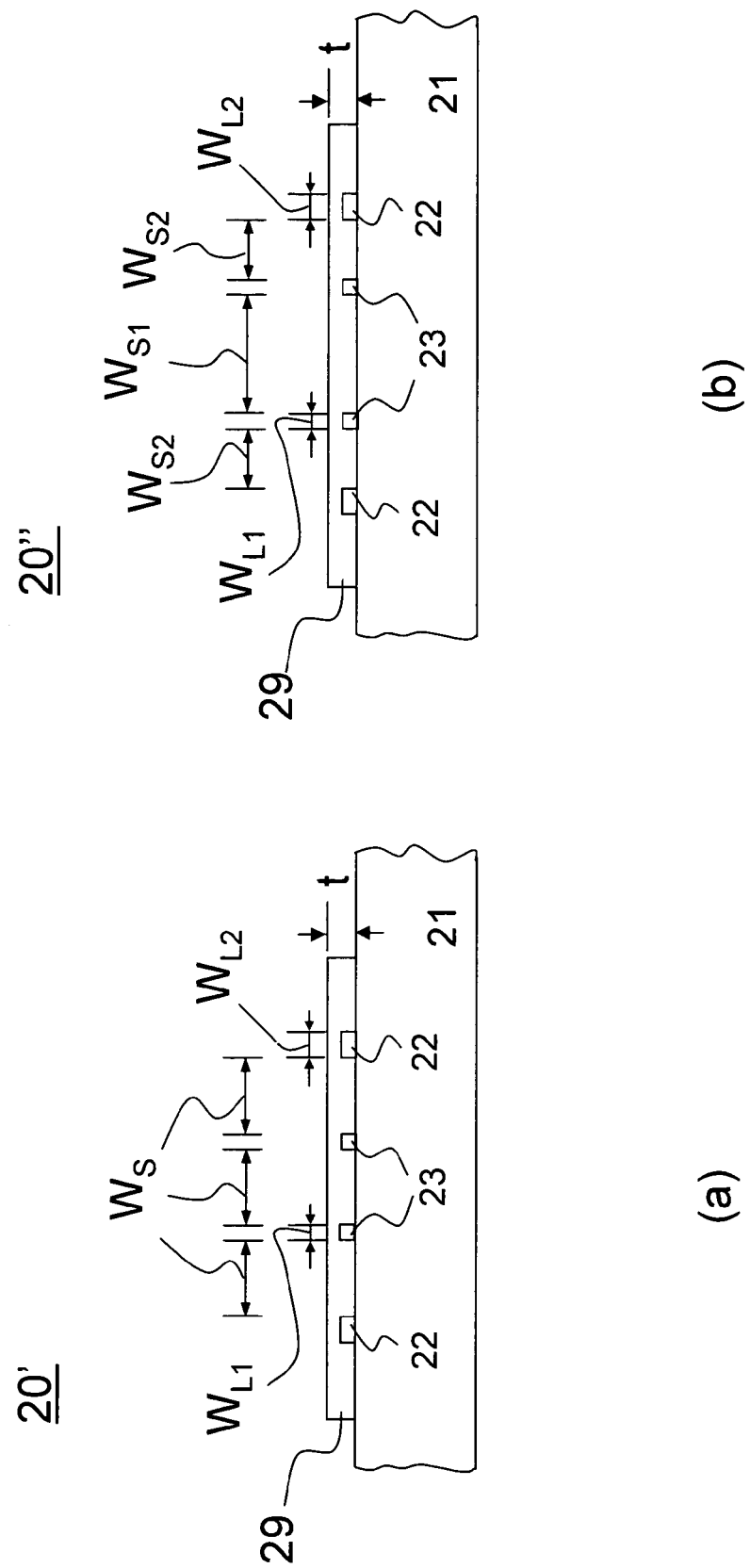
FIG. 3 (a) shows a schematic cross-sectional view of a four-line structure (20') with different line widths, and (b) shows the cross-sectional view of a four-line structure (20") with different line widths and different spacings.

Although in FIG. 2, the four-line structure (20) has the same line width ($W_L$) and spacing ($W_S$) for all four conducting lines, four-line structures with either different line width or different spacings between adjacent conducting lines can also be constructed for four-terminal resistivity measurement. FIG. 3(a) shows a cross-sectional view of a four-line structure (20') having different line widths. In this structure (20'), the outer line width ($W_{L2}$) of the two outer lines (22) is larger than the inner line width ($W_{L1}$) of the inner lines (23). In FIG. 3(b) a four-line structure (20") is shown to have not only different line widths ($W_{L1}$, $W_{L2}$) but also different spacings. In this structure (20"), the inner spacing ($W_{S1}$) are larger than the outer spacings ($W_{S2}$). When different line widths and or different spacings are used for constructing a four-line structure, the ratio between the inner spacing $Ws_1$ to the inner line width $W_{L1}$ should be greater than 5 (and more preferably between 10 and 20).

Figure 4:
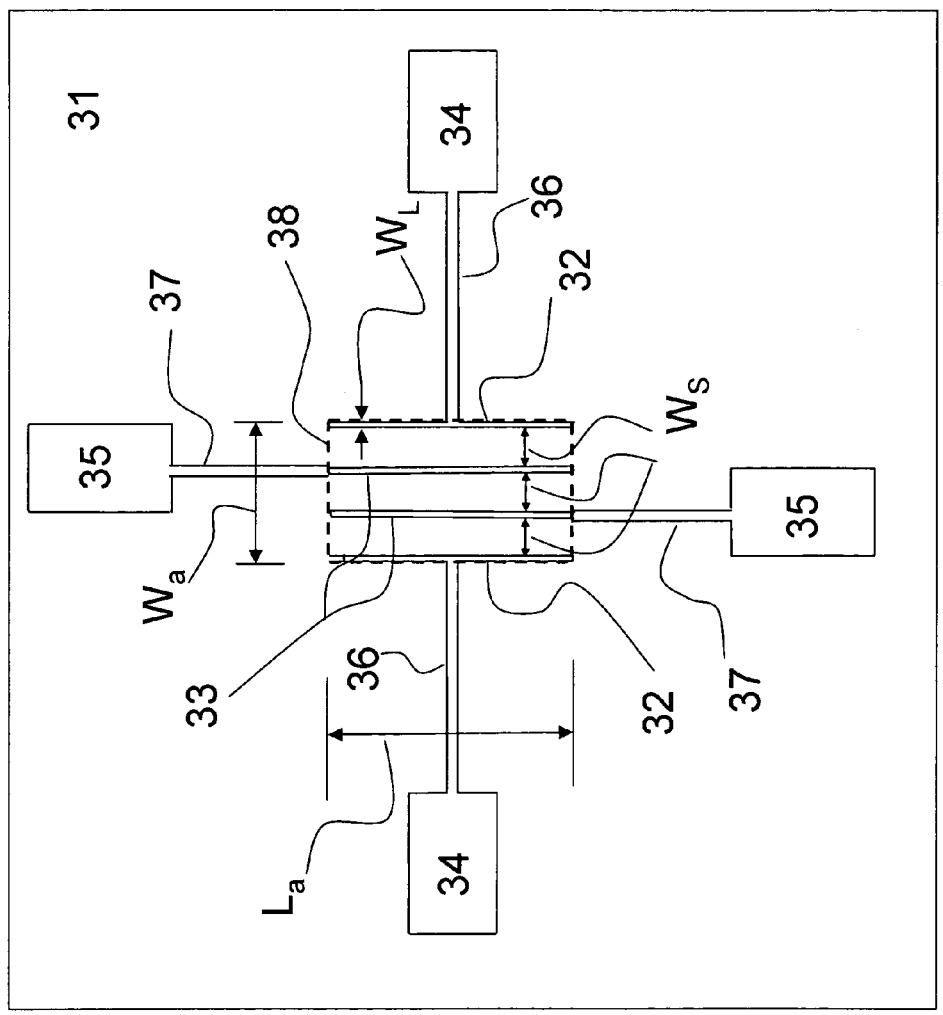
FIG. 4 shows a schematic top view of another four-line structure (30) for four-terminal resistivity measurement.

The four-line structure (20) can have different configurations. FIG. 4 shows a schematic top view of a four-line structure (30) having an altered configuration. This four-line structure (30) is built on an insulating substrate (31), with two outer conducting lines (32) connected to two outer contact pads (34), and two inner conducting lines (33) connected to two inner contact pads (35) through connection sections (36, 37). The connection section (36, 37) can have the same line width of the conducting lines (32, 33) or an increased line width to reduce the resistance of the connection sections (36, 37). The four conducting lines (32, 33) are of the same length ($L_a$) and are parallel to each other. For description purposes, the width ($W_L$) and spacing ($W_S$) between adjacent lines are selected to be the same for all four lines. However, it should be noted that a four-line structure with different line widths and spacings for the four lines can also be constructed for four-terminal resistivity measurement. An active area (38) is defined by the length ($L_a$) of the conducting lines (32, 33) and a width ($W_a$), which is the total width (4 $W_L$+3 Ws) of the four conducting lines (33, 34) and the spacings in between.

The substrate (31) can be selected from any non-conducting substrates including glass plates, ceramic, plastic plates, plastic sheets etc. It can also be semiconductors or metal substrates with an insulating coating on top. The materials for the four conducting lines (32, 33) can be selected from a group of metals, like gold (Au), silver (Ag), titanium (Ti), aluminum (Al), copper (Cu), and indium (In). They can also be selected from a group of metal oxides, including ITO, ZnO, CdS and their combinations. The selection should be made to achieve the smallest contact resistance between the semiconductor and the conducting lines.

The semiconductor thin film can be applied onto (30) by vacuum deposition methods, including thermal evaporation, sputtering, chemical vapor deposition and molecular beam epitaxial, or by non-vacuum methods, including spin coating, spray, screen printing, ink jet printing and chemical bath deposition. The semiconductor film to be tested should cover at least the active area (38) and the thickness (t, refer to FIG. 2(b)) of the semiconductor film (29) should be much smaller than either the length ($L_a$) or the width ($W_a$) of the active area (38). In order for the measurement to be accurate, the ratio of the spacing ($W_S$) to the line width ($W_L$) should be greater than 5 (more preferably between 10 and 20). When different line widths and spacings are used for the conducting lines, the ratio between the inner spacing (refer to $W_{S1}$, FIG. 3) and the inner line width ($W_{L1}$, FIG. 3) should be greater than 5 (preferably between 10 and 20).

Figure 5:
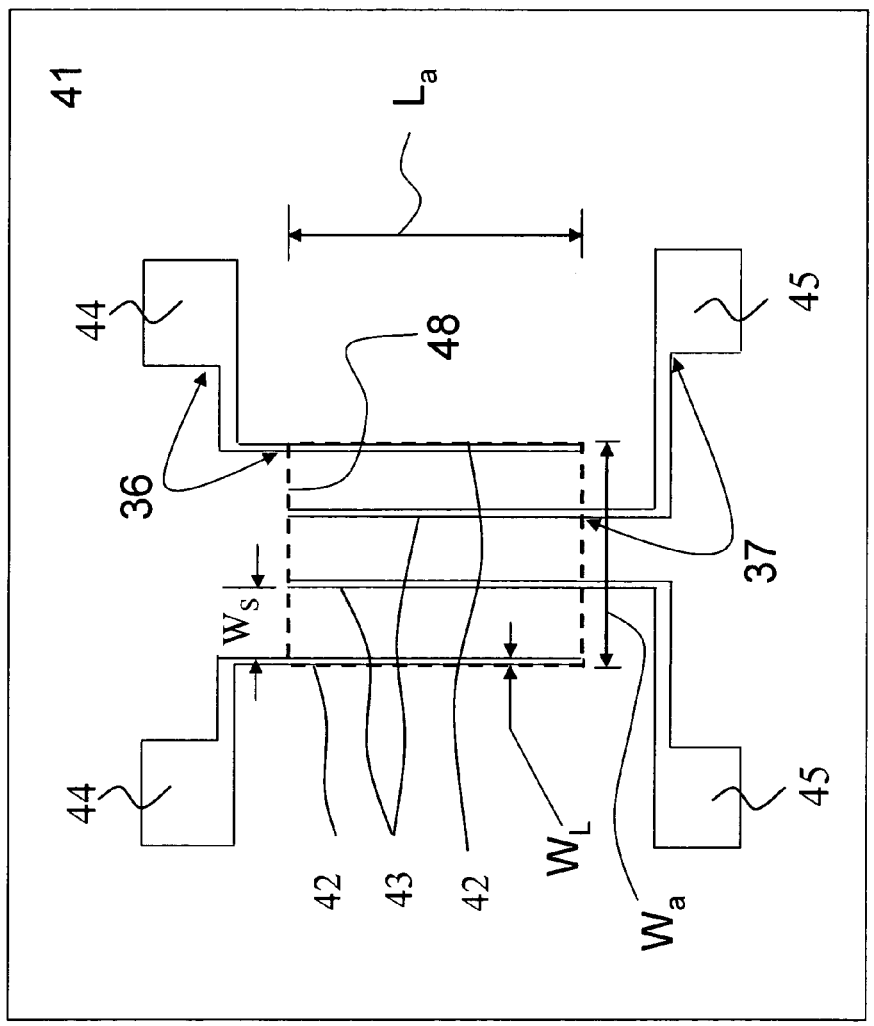
FIG. 5 shows a schematic top view of yet another four-line structure (40) for four-terminal resistivity measurement.

FIG. 5 shows another four-line structure (40) with yet another altered configuration, where on an insulating substrate (41), two outer conducting lines (42) and two inner conducting lines (43) are connected to two outer contact pads (44) and two inner contact pads (45) through connection sections (46, 47) respectively. The four conducting lines are parallel to each other and are of the same length ($L_a$) and width ($W_L$) and with an equal spacing ($W_S$). The active area (48) is defined by the length ($L_a$) of the conducting lines (42, 43) and a width ($W_a$), which is the total width of the four conducting lines (43, 44) and the spacings. In a four-line structure (40) having the same width and spacing for all four lines, $W_a$=4 $W_L$+3 Ws.

The substrate (41) can be selected from a group of electrically insulators including glass plates, ceramic, plastic plates, plastic sheets etc. It can also be semiconductors or metal substrates with an insulating coating on top. The four conducting lines (42, 43) can be selected from a group of metals or a group of metal oxides. The selection should be made to achieve the smallest contact resistance between the semiconductor and the conducting lines.

Semiconductor thin films can be applied onto the four-line structure (40) by vacuum deposition methods, including thermal evaporation, sputtering, chemical vapor deposition and molecular beam epitaxial, or by non-vacuum methods, including spin coating, spray, screen printing, ink jet printing and chemical bath deposition. The semiconductor film to be tested should cover at least the active area (48) and the thickness of the semiconductor film should be much smaller than either the length ($L_a$) or the width ($W_a$) of the active area (48). In order for the measurement to be accurate, the ratio of the spacing ($W_S$) to the line width ($W_L$) should be greater than 5 (more preferably between 10 and 20). When different line widths and spacings are used for the four conducting lines, the ratio between the inner spacing (refer to $W_{S1}$, FIG. 3) and the inner line width ($W_{L1}$, FIG. 3) should be greater than 5 (preferably between 10 and 20).

Multi-Line Structures for Four-Terminal Resistivity Measurement

Figure 6:
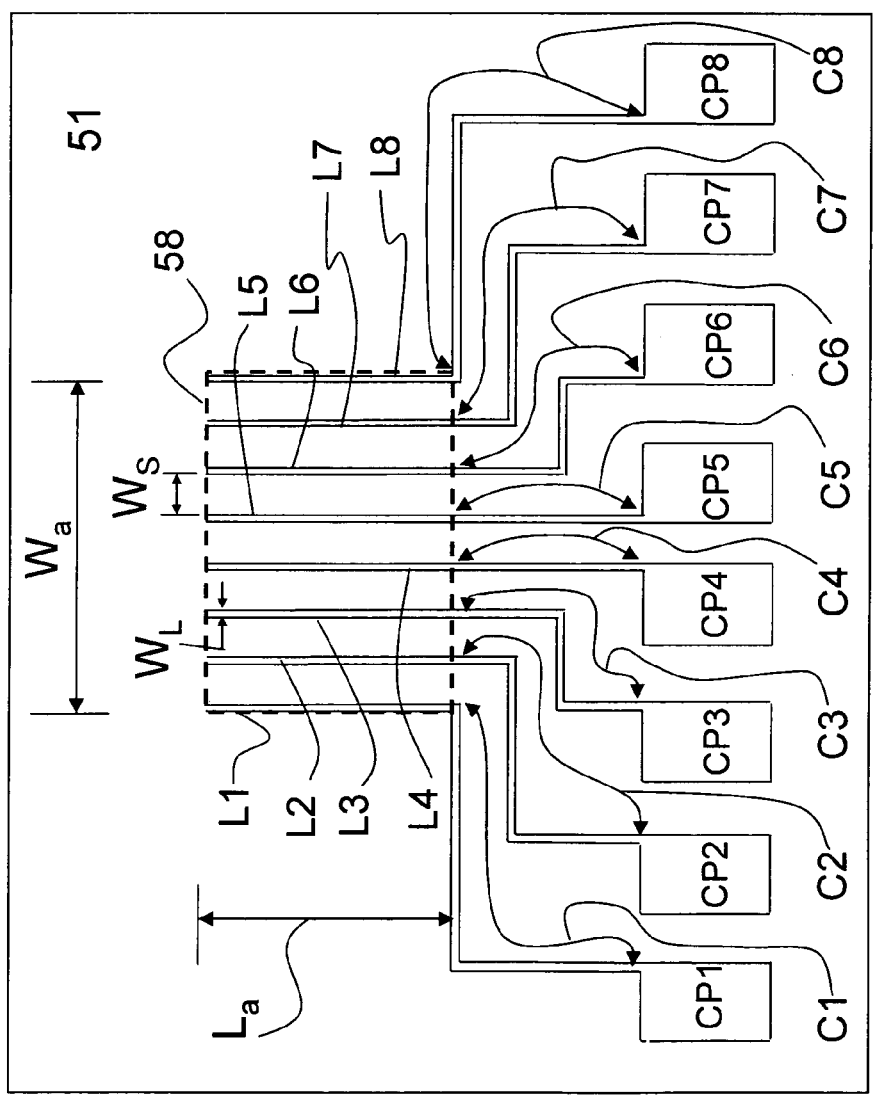
FIG. 6 shows a schematic top view of a multi-line structure (50) for four-terminal resistivity measurement according to another embodiment of the invention.

The four-line structures disclosed in FIGS. 2, 4 and 5 can be expanded to have more than four conducting lines and to form a multi-line structure (50) according to another embodiment of the invention. As shown in FIG. 6, on an insulating substrate (51) eight parallel conducting lines (L1, L2, L3, L4, L5, L6, L7 and L8) of the same length ($L_a$) and width ($W_L$) are equally spaced with a spacing ($W_S$). The eight conducting lines (L1, L2, L3, L4, L5, L6, L7 and L8) are connected to contact pads (CP1, CP2, CP3, CP4, CP5, CP6, CP7 and CP8) through connection sections (C1, C2, C3, C4, C5, C6, C7 and C8) respectively. An active area (58) is defined by a width ($W_a$) and a length ($L_a$), which is equal to the length of the conducting lines.

The substrate (51) can be selected from a group of electrical insulators including glass plates, ceramic, plastic plates, plastic sheets etc. It can also be semiconductors or metal substrates with an insulating coating on top. The eight conducting lines (L1~L8) can be constructed from materials selected from a group of metals or a group of metal oxides. The materials if the conducting lines should be selected to achieve the smallest contact resistance between the semiconductor and the conducting lines. The conducting lines can be formed by a vacuum deposition process followed by a lift-off or an etching process. The lines can also be prepared by a non-vacuum method. The thickness of the conducting lines should be between 0.1 and 10 µm, preferable between 0.5 to 5 µm. This thickness should be selected to provide a small enough resistance for all of the conducting lines.

Semiconductor thin films can be applied onto the multi-line structure (50) by a vacuum deposition method or a non-vacuum method. The semiconductor film to be tested should cover at least the active area (58) and the thickness of the semiconductor film should be much smaller than either the length ($L_a$) or the width ($W_a$) of the active area (58). In order for the measurement to be accurate, the ratio of the spacing ($W_S$) to the line width ($W_L$) should be greater than 5 (more preferably between 10 and 20).

Although the same line width and the same spacing are used to construct the multi-line structure (50), it should be noted that multi-line structure with different line widths and or different spacings can also be constructed for four-terminal resistivity measurements. For multi-line structures using different line widths and or different spacings, the ratio of the inner spacing to the inner line width for each four-terminal measurement should be greater than 5 (preferably between 10 and 20).

The multi-line structure (50) in FIG. 6 can be separated into numbers of four-line substructures, which are defined by a group of any four parallel conducting lines in the multi-line structure (50). There are two types of substructures: adjacent substructures and non-adjacent substructures. The adjacent substructures are formed by four adjacent conducting lines. For example, one of the adjacent four-line substructures is formed by (L1), (L2), (L3) and (L4), and another is formed by (L5), (L6), (L7) and (L8). The central four lines (L3, L4, L5 and L6) of (50) form another adjacent four-line substructure. One additional adjacent four-line substructure is formed by (L2), (L3), (L4) and (L5), and yet another is formed by (L4), (L5), (L6) and (L7).

The non-adjacent four-line substructures are formed by a group of four lines of which at least two lines are not adjacent. There are many possibilities to form a non-adjacent four-line substructure. However, to simplify description in this invention, we will discuss only one type of the non-adjacent four-line substructures—the ones that are formed between the two outmost lines (L1, L8) and a pair of adjacent lines. For example, one such non-adjacent four-line substructure is formed by (L1), (L2), (L3) and (L8) and another is formed by (L1), (L5), (L6) and (L8), where (L2) and (L3), (L5) and (L6) are adjacent.

The multi-line structure (50) in FIG. 6 will allow one to carry out four-terminal resistivity measurements on any adjacent four-line substructures in the multi-line structure (50) so long as the two outer terminals of the adjacent four-line substructure are used to supply the current and the voltage between the two inner terminals are measured to calculate the resistivity of the film. For example, a current can be applied through contact pads (CP1) and (CP4) and the voltage between (CP2) and (CP3) can be measured to calculate the resistivity between (L3) and (L4); or a current can be applied through contact pads (CP3) and (CP6) and voltage between (CP4) and (CP5) can be measured to calculate the resistivity between lines (L4) and (L5). In a similar way, a current can also be applied through contact pads (CP5) and (CP8) and voltage between (CP6) and (CP7) can be measured to calculate the resistivity between lines (L6) and (L7). There are totally five different adjacent four-line substructures in (50). By carrying out all five measurements, one can map out the resistivity values across the active region (58) hence study the resistivity uniformity of the semiconductor films across the semiconductor sample.

Uniformity study is very important for films prepared by a vacuum method. During the deposition of a semiconductor film using a vacuum method, there is always unavoidable compositional deviation from the desired value at certain places along and across the substrate, especially over a relatively large area. Such deviation will cause the properties of the semiconducting film to vary and hence affect the performance of the devices. Other than the above-described method, uniformity of a semiconductor thin film can also be investigated by carrying out resistivity measurements between non-adjacent four-line substructures. For all of the resistivity measurements, the two outmost lines (L1, L8) are used to supply current to the semiconductor film and the voltage between any two adjacent inner lines (e.g. L2 and L3, L3 and L4, L4 and L5, L5 and L6, L6 and L7) is measured to deduce the resistivity of the film between the corresponding inner lines. The measured voltages (and hence the resistivity) for a uniform film should be essentially the same between any pair of adjacent inner lines because of the same spacing ($W_S$) and length ($L_a$) of any given adjacent lines and because of the same electric current flowing through the semiconductor film. Contrarily, large variations in the measured voltages indicate non-uniformity in the semiconductor film.

The uniformity can also be studied by measuring resistance between lines that are not adjacent to each other, for example between (L2) and (L4) and compare it with the resistance measured between two adjacent lines, for example between (L2) and (L3) or between (L3) and (L4). This method can only be used if the ratio between the spacing ($W_S$) and the line width ($W_L$) is very large. When $W_S \gg W_L$, the distance between lines (L2) and (L4) ($d_{2,4}$, not shown in FIG. 6) is approximately twice of that between lines (L2) and (L3) ($d_{2,3}$, not shown), namely $d_{2,4} = 2 \cdot W_S +$ $W_L \approx 2W_S = 2d_{2,3}$. Considering that the contact resistance between the semiconductor film and metallic line (L3) is the same as that between the semiconductor film and the metallic line (L4), one can readily come to the following conclusion. For a uniform semiconductor film, the resistance contributed from the semiconductor film between (L2) and (L4) (total resistance subtracting the total contact resistance) should be approximately twice of that between (L2) and (L3) or between (L3) and (L4). If not, the film is considered to be not uniform.

Figure 7:
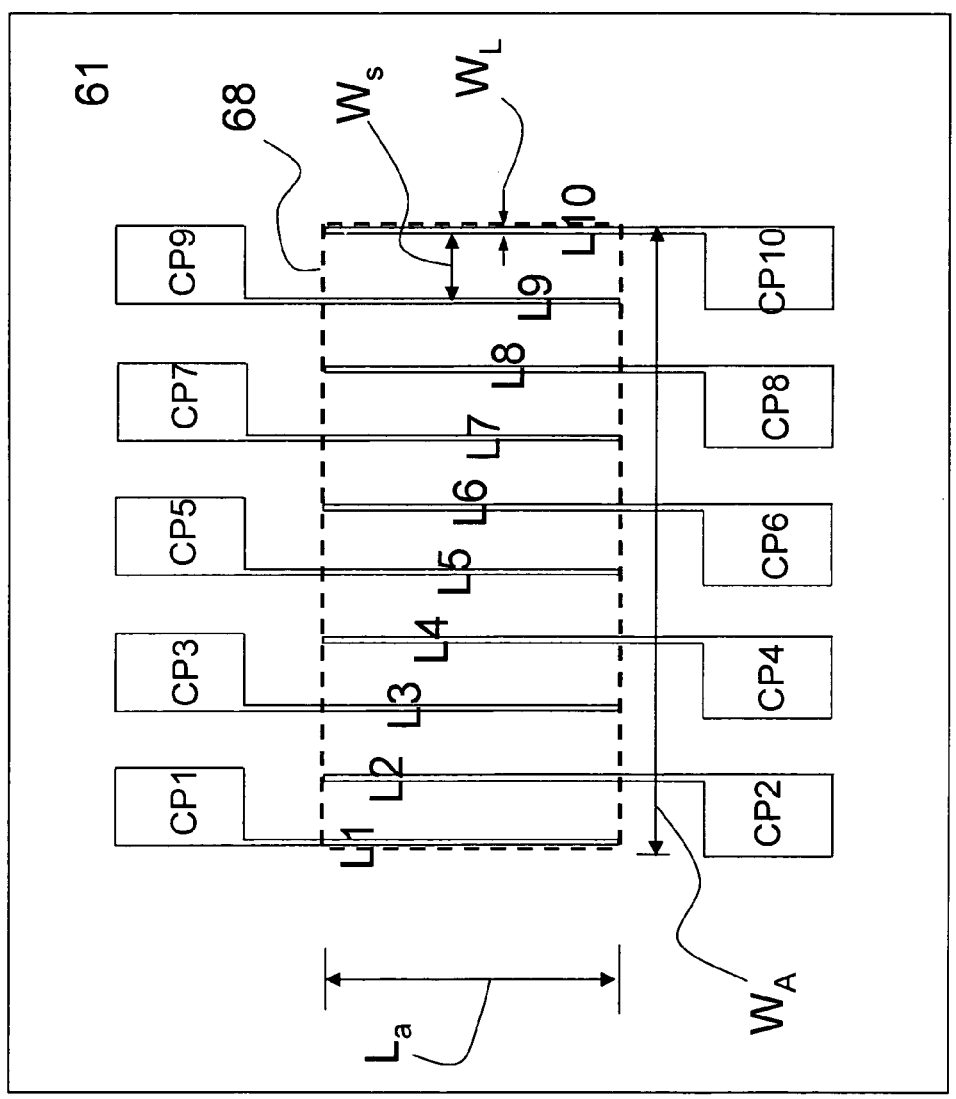
FIG. 7 shows a schematic top view of another multi-line structure (60) for four-terminal resistivity measurement.

The multi-line structure (50) disclosed in FIG. 6 can be modified to have a different arrangement (60). As shown in FIG. 7, on an insulating substrate (61) ten parallel conducting lines (L1, L2, L3, L4, L5, L6, L7, L8, L9 and L10) of the same length ($L_a$) and width ($W_L$) are equally spaced with a spacing of ($W_S$). The ten conducting lines (L1, L2, L3, L4, L5, L6, L7, L8, L9 and L10) are connected to their respective contact pads (CP1, CP2, CP3, CP4, CP5, CP6, CP7, CP8, CP9 and CP10). An active area (68) is defined by a width ($W_a$) and a length ($L_a$), which is equal to the length of the metallic lines (L1~L10).

Organic semiconductor thin films can be applied onto the multi-line structure (60) by a vacuum deposition method or a non-vacuum method. The semiconductor film to be tested should cover at least the active area (68) and the thickness of the semiconductor film should be much smaller than either the length ($L_a$) or the width ($W_a$) of the active area (68). In order for the measurement to be accurate, the ratio of the spacing ($W_S$) to the line width ($W_L$) should be greater than 5 (more preferably between 10 and 20).

Although the same line width and the same spacing are used to construct the multi-line structure (60), it should be noted that multi-line structure with different line widths and or different spacings can also be constructed for the four-terminal resistivity measurements. For multi-line structures using different line widths and or different spacings, the ratio of the inner spacing to the inner line width for each four-terminal measurement should be greater than 5 (preferably between 10 and 20).

The multi-line structure (60) in FIG. 7 will allow one to carry out four-terminal resistivity measurements on any adjacent four-line substructures in (60) so long as the two outer terminals are used to supply the current and the voltage between the two inner terminals are measured to calculate the resistivity of the film. For example, a current can be applied through contact pads (CP1) and (CP4) and the voltage between (CP2) and (CP3) can be measured to calculate the resistivity between lines (L2) and (L3). A current can also be applied through contact pads (CP3) and (CP6) and voltage between (CP4) and (CP5) can be measured to calculate the resistivity between lines (L4) and (L5). In a similar way, a current can also be applied through contact pads (CP5) and (CP8) and voltage between (CP6) and (CP7) be measured to calculate the resistivity between lines (L6) and (L7). There are totally seven adjacent four-line substructures in the multi-line structure (60). By carrying out all seven measurements, one can map out the resistivity values across the active region (68) hence study the resistivity uniformity of the semiconductor films across the sample.

The uniformity of a semiconductor films can also be investigated by carrying out resistivity measurements between non-adjacent four-line substructures in multi-line structure (60). For all of the resistivity measurements, the two outmost lines (L1, L10) are used to supply current to the semiconductor film and the voltage between any two adjacent inner lines (e.g. L2 and L3, L3 and L4, L4 and L5, L5 and L6, L6 and L7, L7 and L8, L8 and L9) is measured to deduce the resistivity of the film between corresponding inner lines. The measured voltages (and hence the resistivity) for a uniform film should be essentially the same between any pair of adjacent inner lines because of the same spacing ($W_S$) and length ($L_a$) and because of the same electric current flowing through the semiconductor film. Contrarily, large variations in the measured voltages indicate non-uniformity of the semiconductor thin film.

Four-Terminal Resistivity Measurement Methods

Although the four-line and multi-line structures and the four-terminal resistivity measurement methods are invented to solve problems mainly existing for organic semiconductors, the same structures and four-terminal methods can be advantageous for inorganic semiconductor materials as well due to the possibility to study the uniformity of the semiconductor thin film and the flexibility in selecting a better material to reduce the contact resistance.

With the intention of simplifying the description, the equipment setup and the procedure for four-terminal resistivity measurement will be described based on the four-line structure (20) given in FIG. 2. However, it should be noted that the same description can be used to illustrate measurements carried out on any four-line substructure in a multi-line structure.

Figure 8:
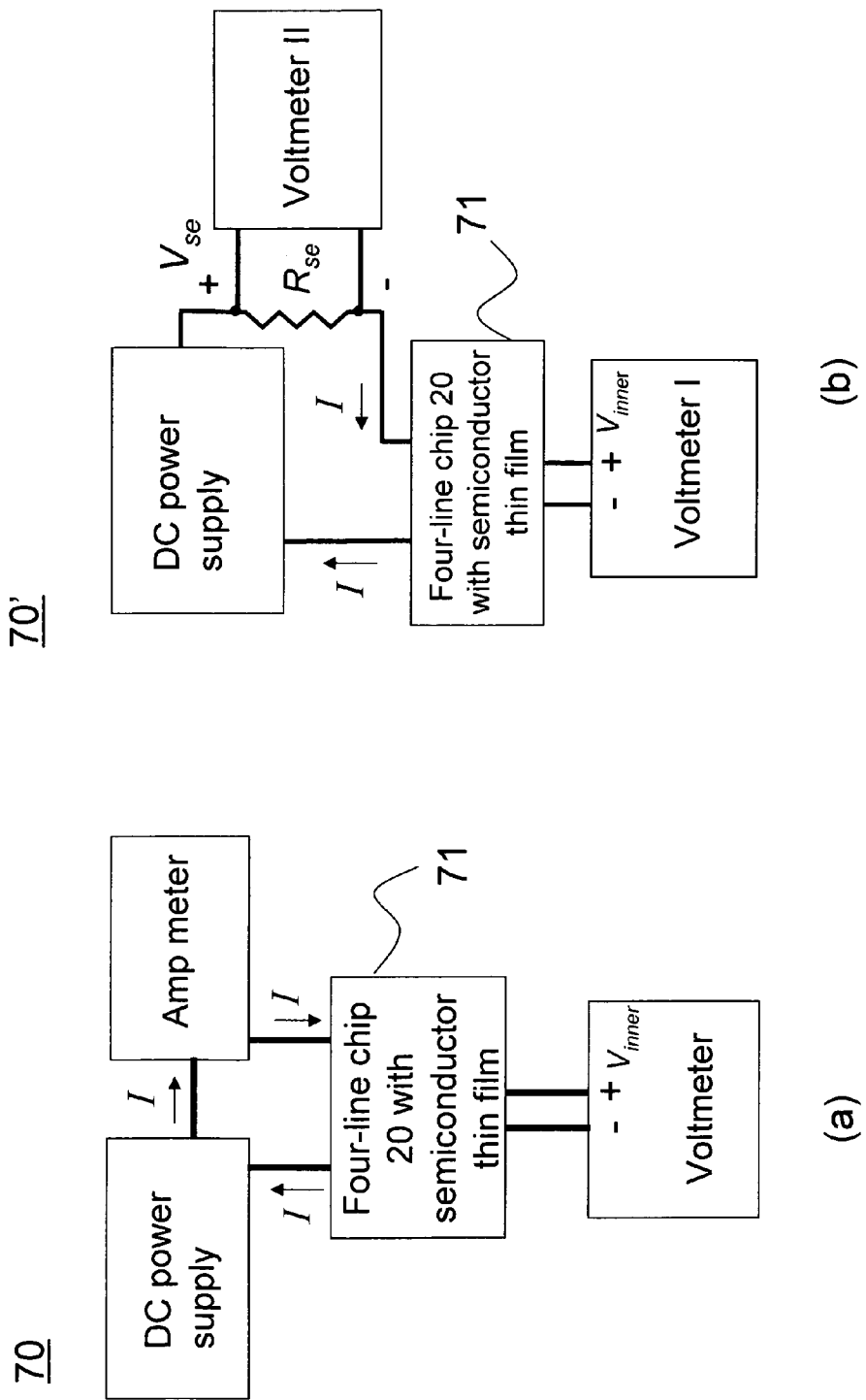
FIG. 8 schematic diagrams showing the equipment setups (70, 70') for resistivity measurement using the four-terminal method.

To measure the resistivity (or conductivity) of a semiconductor using the four-terminal methods, a setup (70) as illustrated in FIG. 8(a) can be used, where a DC power supply is used to supply the current (I) to the two outer lines of the testing sample (71), which consists of the four-line structure (20, in FIG. 2) coated with the semiconductor thin film to be tested. An amp meter is connected in series with the DC power supply to determine the current (I). A voltmeter with high input impedance is connected to the two inner contact pads (25, refer to FIG. 2(a)) of the testing sample (71) to measure the voltage ($V_{inner}$) across the two inner lines (23, refer to FIG. 2(a)). The resistivity measurement can also be done by using two voltmeters, as shown in setup (70') in FIG. 8(b)), where the current (I) is deduced from the voltage ($V_{se}$) measured across a series resistor ($R_{se}$) by a second voltmeter (voltmeter II):

$$I = \frac{V_{se}}{R_{se}} \qquad (3)$$

Because the resistance between the two inner contact pads (25, refer to FIG. 2(a)) of the testing sample (71) is normally very high (up to a few tens of GΩ), one needs to supply a large enough voltage to the outer contact pads of the testing sample (71) to generate a large enough current (I). In order to accurately measure the voltage ($V_{inner}$) between the two inner lines and not to cause any current to flow between the inner pads and the voltmeter I, the input impedance of voltmeter I should be very high. Similarly, the input impedance of voltmeter II should be very high as well. More preferably, voltmeter I and II should be replaced by electrometers.

Figure 9:
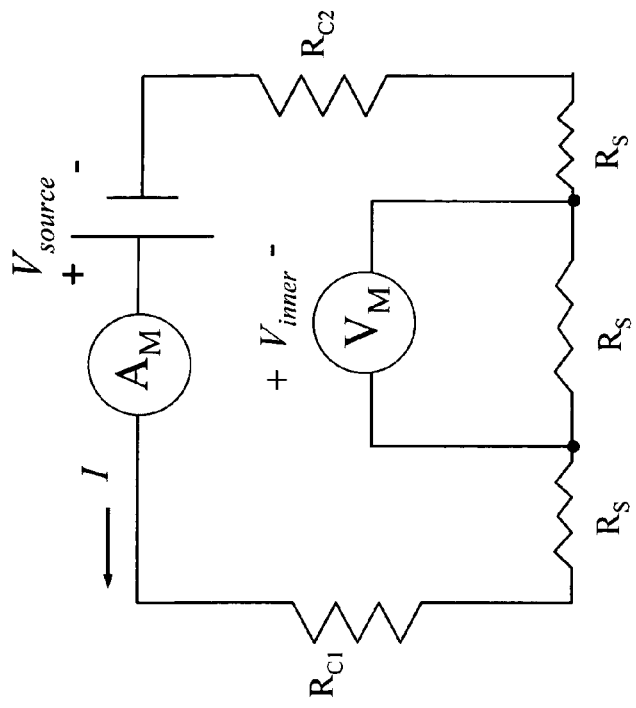
FIG. 9 equivalent circuit (80) and a simplified circuit (81) for the resistivity measurement setup (70) shown in FIG. 8(a).
Figure 9:
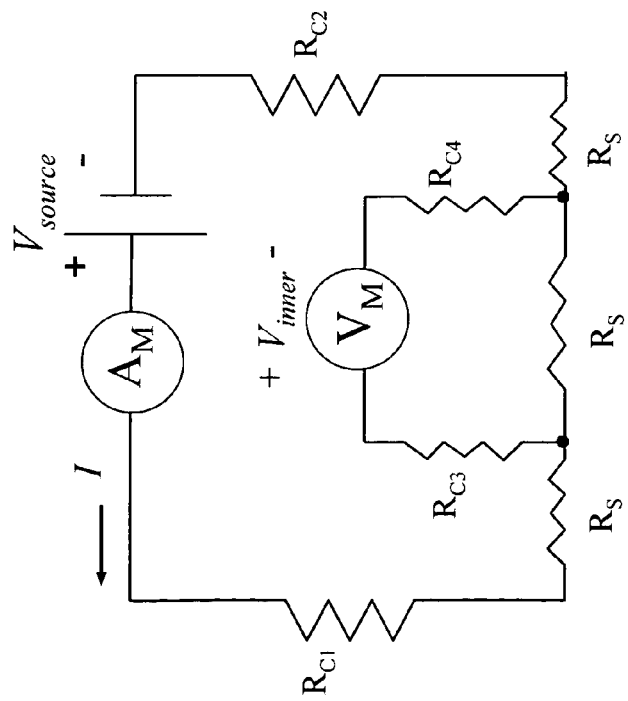

The equivalent electrical circuit (80) of the testing setup (70) is given in FIG. 9(a), where $V_{source}$ is the total output voltage from the DC power supply, $V_{inner}$ is the voltage between the inner two conducting lines, ($A_M$) and ($V_M$) represent the amp meter and the voltmeter respectively. The current (I) flowing into the testing sample (71) is measured by the amp meter ($A_M$) and the voltage $V_{inner}$ is measured by the voltmeter ($V_M$). Resistor ($R_S$) represents the resistance contributed from each semiconductor segment sandwiched between two adjacent conducting lines. Since there are three such segments, there are three identical resistors ($R_S$).

Because it is impossible to find a conducting film (metal or metal oxide) to form a good ohmic contact to an organic semiconductor, fairly large contact resistance normally exists between the organic semiconductor and the conducting lines (22, 23 in FIG. 2(*a*)). In order to obtain the actual resistance of an organic semiconductor film, it is required to extract the contact resistance from the measured value. The resistors $R_{C1}$, $R_{C2}$, $R_{C3}$ and $R_{C4}$ in FIG. 8(*a*) represent the contact resistance between the semiconductor thin film and each of the four conducting lines (L1, L2, L3, and L4, refer to FIG. 2(*a*)). By defining a total contact resistance $R_C = R_{C1} + R_{C2} = R_{C3} + R_{C4}$, the total resistance ($R_{outer}$) between the two outer contact pads of the sample (71) is given by $$R_{outer} = R_{C1} + R_{C2} + 3R_S = R_C + 3R_S \quad (4)$$

And the total resistance ($R_{inner}$) between the two inner contact pads of sample (71) including the two contact resistance $R_{C3}$, $R_{C4}$ and the resistance ($R_S$) of the central semiconductor segment is:

$$R_{inner} = R_{C3} + R_{C4} + R_S = R_C + R_S \quad (5)$$

Assuming the input impedance ($R_{input}$, not shown) of the voltmeter ($V_M$) is high enough so that $R_{input} + R_{C3} + R_{C4} \gg R_S$, and the current flow through the voltmeter ($V_M$) is extremely small and can be ignored. Then it is safe to assume that the current flowing through the central semiconductor segment is the same as that flowing through the other two segments. Because of this assumption, the equivalent circuit (80) in FIG. 9(*a*) can be simplified to (81) shown in FIG. 9(*b*), where $R_{C3}$ and $R_{C4}$ are absent. Therefore, the total resistance ($R_{inner}$) between the two inner contact pads (25, FIG. 2(*a*)) can be calculated directly from the measured voltage ($V_{inner}$) and the current (I) flowing through the semiconductor sample:

$$R_{inner} = R_S = \frac{V_{inner}}{I} \quad (6)$$

By knowing the thickness (t) of the semiconductor thin film, the length ($L_a$) and the width ($W_S$) of the four-line structure (refer to FIG. 2) one can easily calculate the resistivity (ρ) of the semiconductor thin film:

$$\rho = R_S \frac{w_S \cdot t}{L_a} \approx \frac{V_{inner}}{I} \cdot \frac{w_S \cdot t}{L_a} \; \Omega\text{-cm} \quad (7)$$

The conductivity (σ) can then be calculated by:

$$\delta = \frac{1}{\rho} \; \text{S/cm} \quad (8)$$

The total contact resistance ($R_C$) can be calculated using the following equation:

$$R_C = R_{C1} + R_{C2} = \frac{V_{source}}{I} - 3R_S = \frac{V_{source}}{I} - 3R_{inner} \quad (9)$$

From the deduced total contact resistance ($R_C$), it can be determined whether or not the material used for the four-line structure is suitable for the semiconductor studied. If the contact resistance ($R_C$) obtained is exceptionally large, one can consider to choose a different material with a different work function to construct the four-line structure, depending on the type of conducting carriers in the semiconductor material and its work function. Although it is not possible to eliminate completely the contact resistance $R_C$, a better matched material will reduce the total contact resistance and make the measurement procedure much easier to perform.

Although it is convenient to use four-line or multi-line structures with a pre-selected conducting line length and spacing for all semiconductors, it is beneficial to select the length and the spacing of a structure according to the semiconductor material to be studied. For example, a longer length and or a narrower spacing should be chosen to construct the multi-line structures for semiconductor materials with a very high resistivity. The increase in length and decrease in spacing reduce the resistance between the inner and outer lines and therefore can make the measurements easier to handle. However, when the spacing is reduced, the line width has to be reduced as well to maintain a larger than 5 ratio between the spacing and the line width. The reduction in line width reduces the contact area and in turn increases the contact resistance. Hence, all factors have to be taken into consideration before determining the parameters of a four-line or a multi-line structure.

EXAMPLES

In the following examples we present resistivity measurement results for some typical organic semiconductors using the four-line structure and the four-terminal measurement methods.

1. Four-Line Testing Chip

The four-line structure testing chips used in the examples are fabricated on glass slides but one should not limit oneself to glass substrates only.

Four-line testing chip parameters used in the examples are:
Substrate: glass slide
Substrate dimension: 1.1×1.1 $cm^2$
Substrate thickness: 1 mm
Metallic liner length: 3.5 mm
Metallic line width: 3.0 μm
Spacing between fingers: 50 μm
Metals used: Au, Ag, Ti, Al
Resistance of metallic lines: <1 ohm 2. Four-Terminal Resistivity Measurement In this section, we will give a few examples of four-terminal resistivity measurements carried out on several typical organic semiconductor materials. In this work, we have employed a Hewlett Packard DC power supply (mode no. 6200B) and two HP multi-meters (model no. 34401 A) with an input impedance>10 GΩ. The setup (70′) illustrated in FIG. 8(*b*) is used for the measurements.

2.1 PEDOT

PEDOT is widely used as a hole-transport layer in organic light emitting diodes. Four-line testing chips made of gold (Au) film are used for this experiment. PEDOT solution (2.8 wt % of Sigma PEDOT dissolved in water) is spin coated on to the testing chips at a spin rate of 1,500 rpm. The thickness of the material is determined using a Dektak surface profile system to be about 94 nm. In this experiment, the series resistor used is 1.2 MΩ and the DC voltage output from the power supply is set between 3 to 4 volts. The resistance values between the two inner contact pads are calculated to be in a range of 1 to 1.7 MΩ. Conductivity values between $9.2 \times 10^{-4}$ to $1.5 \times 10^{-3}$ S/cm are obtained on a number of samples. The total contact resistance $R_S$ is in the range from 1 to 2.4 MΩ.

2.2 P3HT

Figure 10:
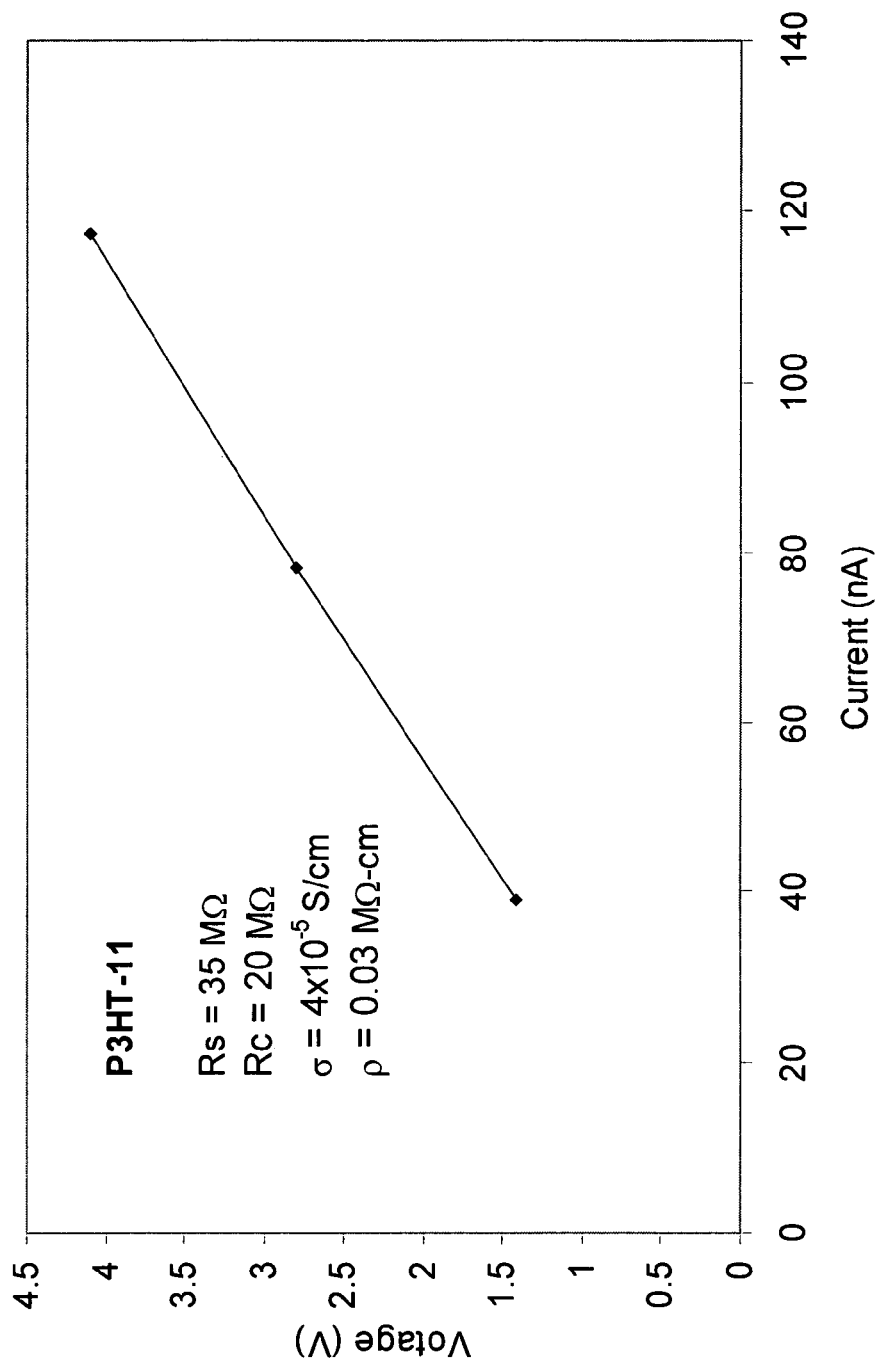
FIG. 10 measured voltage between the two inner terminals plotted against the measured electric current to the two outer terminals for a P3HT sample.

P3HT is also used as a hole-transport layer. In this work, the material is obtained from Rieke Metal. P3HT thin films are prepared from a 2 wt % solution at a spin rate of 1,000 rpm. Au four-line testing chips are used for P3HT. The thickness of the P3HT thin films is measured using a Dektak surface profile measuring system to be about 100 nm. A larger series resistance (8 MΩ) is used this time because of a smaller current, so that the voltage reading across the series resistor is large enough to be accurate. The DC voltage output from the power supply is set between 10 to 30 volts. FIG. 10 shows the voltage ($V_{inner}$) between the inner contact pads plotted against current (I) for sample P3HT-11, where the relationship follows a straight line. In Table 1, the measurement results on a set of four P3HT samples are listed. Of the four samples, P3HT-8 and 9 are as-purchased and unpurified samples while P3HT1-10 and 11 are samples that have gone through a purification process. The measured ($R_S$) values between the two inner contact pads are seen in the range of 50 to 80 MΩ for the as-purchased P3HT samples and 35 to 45 for the purified P3HT samples. The resistivity values for the unpurified samples are between 0.04 to 0.06 MΩ-cm and the purification process reduces these values to 0.02 to 0.03 MΩ-cm. The conductivity for the unpurified samples are $1.7 \times 10^{-5}$ to $3.2 \times 10^{-5}$ S/cm and for the purified samples are between $3.1 \times 10^{-5}$ and $4.1 \times 10^{-5}$ S/cm. Please note that the conductivity of this material is about two orders of magnitude lower than that of the PEDOT films. The total contact resistance $R_C$ is in a range of 19 to 46 MΩ. This higher total contact resistance (comparing to the PEDOT samples) indicates a poorer contact between the Au film and the P3HT films.

Table 1 Resistivity measurement results on four P3HT samples.

2.3 MEH/PPT

MEH/PPT is a popular red polymer for PLED application. In this work, the material is synthesized in Organic Vision Inc. When a 2 wt % solution is spin coated onto Au testing chips at a rate of 1,000 rpm, the thickness of the MEH/PPT thin films is measured to be about 100 nm. The series resistor used is 8 MΩ and the DC voltage output from the power supply is set between 10 to 20 volts. The resistance values between the two inner contact pads are measured to be in the range of 17 to 24 GΩ, from which resistivity values of 12.1 to 17 MΩ-cm and conductivity values of $5.9 \times 10^{-8}$ to $8.3 \times 10^{-8}$ S/cm are obtained. Please note that the conductivity of red polymer is even lower than that of P3HT (about three orders of magnitude lower). For these samples, the total contact resistance $R_C$ is in the range of 4.8 to 8.0 GΩ which is higher than that the PEDOT and the P3HT samples. This high contact resistance, which is comparable with the input impedance of the multimeter, indicates an even poorer contact between the Au film and the MEH/PPT films. Although the above-mentioned results are obtained by multimeters, because of the large resistivity and large contact resistance, an electrometer with input impedance significantly greater than 1000 GΩ should be used to guarantee there is no current flow into the multimeter.

2.4 Alq$_3$

Alq$_3$ is the most popular small molecule organic material for OLED application. We have used commercial Alq$_3$ from Toyo Inc. to carry out preliminary resistivity measurements. The Alq$_3$ thin films are deposited using a thermal evaporation method onto the testing chips made of Au, Ag and Ti; the later two have lower work function than Au. The thickness of the Alq3 thin films is controlled to 200 nm using a thickness monitor. In this experiment, the series resistance used is 1.2 GΩ. The DC voltage output from the power supply is set to be 10 volts. The resistance values between the two inner contacts are measured to be in the range of 23 to 36 GΩ, from which resistivity values are obtained to be in the range of 32 to 50 MΩ-cm and the corresponding conductivity is in the range of $2.0 \times 10^{-8}$ to $3.2 \times 10^{-8}$ S/cm. The total contact resistance $R_C$ is very high for these samples (about 60 GΩ for Ag, 70 for Ti and more than 100 for Au). This particularly high contact resistance is higher than the input impedance of the multimeters and indicates a very poor contact between the metal film (especially Au) and the Alq$_3$ film. The above-mentioned preliminary results are obtained by multimeters. Because of the particularly high resistivity and contact resistance, an electrometer with input

TABLE 1

Resistivity measurement results on four P3HT samples.

|  | RM-8* | | | RM-9* | | | RM-10** | | | RM-11** | | |
|---|---|---|---|---|---|---|---|---|---|---|---|---|
| $V_{source}$ (V) | 5 | 10 | 15 | 5 | 10 | 15 | 5 | 10 | 15 | 5 | 10 | 15 |
| $R_S$ (MΩ) | 85.2 | 81.8 | 81.2 | 50.3 | 51.1 | 52.6 | 44.8 | 46.4 | 45.8 | 36.3 | 35.8 | 35.0 |
| ρ (MΩ-cm) | 0.06 | 0.06 | 0.06 | 0.04 | 0.04 | 0.04 | 0.03 | 0.03 | 0.03 | 0.03 | 0.03 | 0.02 |
| σ ($10^{-5}$ S/cm) | 1.7 | 1.8 | 1.8 | 2.8 | 2.8 | 2.7 | 3.2 | 3.1 | 3.1 | 3.9 | 4.0 | 4.1 |
| $R_C$ (MΩ) | 42 | 38 | 46 | 21 | 23 | 22 | 38 | 31 | 30 | 19 | 20 | 23 |

*as purchased/**purified impedance significantly greater than 1000 GΩ is highly recommended to carry out the resistivity measurements on semiconductor Alq$_3$.

The above-described examples have been given to illustrate the spirit of this invention. Although all of the resistivity measurements in the examples are performed on organic semiconductors, the four-terminal resistivity measurement method may well be used to study the resistivity and resistivity uniformity of inorganic semiconductors. are all it should be noted that the four-terminal method is as effective when used for inorganic semiconductors.

What is claimed is:

1. A multi-line structure for four-terminal resistivity measurement of a semiconductor comprising:
   a substrate,
   at least four parallel conducting lines of an equal length deposited on a front surface of said substrate, each of said conducting lines has a thickness, a line width and a spacing between adjacent conducting lines, wherein said conducting lines and said spacings form an active area, said active area has a width and a length equal to said length of said parallel conducting lines,
   at least four contact pads, each of said contact pads is connected to an end of one of said parallel conducting lines through a connection section, wherein any of four said parallel conducting lines and corresponding contact pads form a four-line substructure, and
   a semiconductor thin film with a thickness covers at least said active area, said thickness of said semiconductor thin film is much smaller than said length or said width of said active area.

2. A multi-line structure for four-terminal resistivity measurement of a semiconductor as defined in claim 1, wherein said substrate is selected from a group comprising: glass substrates, plastic substrates, plastic sheets, ceramic substrates, semiconductor substrates and metal substrates having a dielectric coating.

3. A multi-line structure for four-terminal resistivity measurement of a semiconductor as defined in claim 1, wherein material of said parallel conducting lines is selected from a metal group comprising: Au, Ag, Pt, Al, Cu, Ti, Cr, In, Ni, Sn, Zn, Mo, Sb, W, Fe, Tl and their combinations.

4. A multi-line structure for four-terminal resistivity measurement of a semiconductor as defined in claim 1, wherein material of said parallel conducting lines is selected from a conducting metal oxide group comprising: ITO, ZnO, CdS and their combinations.

5. A multi-line structure for four-terminal resistivity measurement of a semiconductor as defined in claim 1, wherein said parallel conducting lines have the same line width.

6. A multi-line structure for four-terminal resistivity measurement of a semiconductor as defined in claim 1, wherein said parallel conducting lines have different line widths.

7. A multi-line structure for four-terminal resistivity measurement of a semiconductor as defined in claim 1, wherein said thickness of said parallel conducting lines is between 0.1 and 5 µm.

8. A multi-line structure for four-terminal resistivity measurement of a semiconductor as defined in claim 1, wherein all of said spacings between adjacent parallel conducting lines have the same width.

9. A multi-line structure for four-terminal resistivity measurement of a semiconductor as defined in claim 1, wherein all of said spacings between adjacent parallel conducting lines have different widths.

10. A multi-line structure for four-terminal resistivity measurement of a semiconductor as defined in claim 1, wherein a ratio between said spacing to said line width of said parallel conducting lines is greater than 5.

11. A multi-line structure for four-terminal resistivity measurement of a semiconductor as defined in claim 1, wherein said semiconductor thin film is an inorganic semiconductor.

12. A multi-line structure for four-terminal resistivity measurement of a semiconductor as defined in claim 1, wherein said semiconductor thin film is an organic semiconductor.

13. A method for four-terminal resistivity measurement of a semiconductor using a multi-line structure comprising the steps of:
   forming a multi-line structure on a substrate using a conducting material, said multi-line structure comprises at least four parallel conducting lines of equal length and at least four contact pads, each of said parallel conducting lines has a spacing between adjacent lines and is connected to one of said contact pads, wherein all said parallel conducting lines and spacings form an active area with a length and a width, whereas any of four said parallel conducting lines and corresponding contact pads form a four-line substructure,
   forming a semiconductor thin film to cover at least said active area of said multi-line structure, thickness of said semiconductor thin film is much smaller than said length or said width of said active area,
   selecting a four-line substructure in said multi-line structure,
   applying an electrical current to two outer lines of said four-line substructure,
   measure the voltage between two inner lines of said four-line substructure, and
   calculate resistivity of said semiconductor thin film between said two inner lines of said four-line substructure.

14. A method for four-terminal resistivity measurement of a semiconductor using a multi-line structure as defined in claim 13, wherein said substrate is selected from a group comprising: glass substrates, plastic substrates, plastic sheets, ceramic substrates, semiconductor substrates and metal substrates having a dielectric coating.

15. A method for four-terminal resistivity measurement of a semiconductor as defined in claim 13, further comprise a step of selecting said conducting material from a group of metals and metal oxides to reduce the contact resistance between said parallel conducting lines and said semiconductor thin film by.

16. A method for four-terminal resistivity measurement of a semiconductor using a multi-line structure as defined in claim 13, wherein said parallel conducting lines are formed by a process selected from a group comprising: vacuum deposition processes and non-vacuum deposition processes.

17. A method for four-terminal resistivity measurement of a semiconductor as defined in claim 13, further comprises a step of improving said four-terminal resistivity measurement by changing said length and said spacing of said parallel conducting lines in said multi-line structure.

18. A method for four-terminal resistivity measurement of a semiconductor as defined in claim 13, further comprises a step of studying uniformity of said semiconductor thin film by selecting a set of four-line substructures and performing four-terminal resistivity measurements on all selected four-line substructures in said multi-line structure.

19. A method for four-terminal resistivity measurement of a semiconductor as defined in claim 13, wherein said semiconductor thin film is selected from a group comprising: inorganic semiconductors and organic semiconductors.

20. A method for four-terminal resistivity measurement of a semiconductor as defined in claim 13, wherein said semiconductor thin film is deposited by a process selected from a group comprising: vacuum deposition processes and non-vacuum deposition processes.

* * * * *